United States Patent [19]

Baugh et al.

[11] Patent Number: 4,801,743
[45] Date of Patent: Jan. 31, 1989

[54] PROCESS FOR PREPARING CARBOXYLIC ACIDS

[75] Inventors: William D. Baugh; Jawad H. Murib, both of Cincinnati, Ohio

[73] Assignee: National Distillers and Chemical Corporation, New York, N.Y.

[21] Appl. No.: 533,709

[22] Filed: Sep. 19, 1983

Related U.S. Application Data

[63] Continuation of Ser. No. 276,105, Jun. 22, 1981, abandoned.

[51] Int. Cl.$^4$ ............................................. C07C 51/12
[52] U.S. Cl. .................................................... 562/519
[58] Field of Search ............... 562/519, 522; 560/204, 560/206, 207, 232; 549/233, 231

[56] References Cited

U.S. PATENT DOCUMENTS 3,501,518  3/1970  Kutepow II et al. ............... 562/522

FOREIGN PATENT DOCUMENTS 1137163  12/1968  United Kingdom ............... 562/522

Primary Examiner—Nicky Chan
Attorney, Agent, or Firm—Kenneth D. Tremain

[57] ABSTRACT

Allyl alcohol is reacted with carbon monoxide in the presence of a catalytically effective amount of a heterogeneous catalyst composition comprising zero valent palladium and a catalyst promoting amount of hydrogen halide to provide a mixture of products predominantly made up of carboxylic acids containing four and five carbon atoms, e.g., 3-butenoic acid, crotonic acid, butyric acid, isobutyric acid, glutaric acid and methyl succinic acid and possibly minor amounts of other oxygenated compounds such as allyl ether and allyl 3-butenoate.

19 Claims, No Drawings

PROCESS FOR PREPARING CARBOXYLIC ACIDS

This is a continuation of application Ser. No. 276,105, filed on June 22, 1981, now abandoned.

BACKGROUND OF THE INVENTION

1. Field of the Invention

This invention relates to the field of processes for preparing acyclic carboxylic acids and, more particularly, to such processes featuring the reaction of an olefinic compound and carbon monoxide in the presence of palladium-containing catalyst (i.e., carbonylation).

2. Description of the Prior Art

The $C_4$ and $C_5$ carboxylic acids, e.g., 3-butenoic acid (vinylacetic acid), crotonic acid, butyric acid, isobutyric acid, glutaric acid and methyl succinic acid are industrially important compounds useful as intermediates for the manufacture of numerous chemical products. It is known at present that carboxylic acids and/or carboxylic acid esters can be prepared by the reaction of an olefinically unsaturated compound and carbon monoxide (i.e., carbonylation) in the presence of palladium-containing catalysts. U.S. Pat. No. 3,427,344 to Tsuji, et al. describes the reaction of allyl alcohol with carbon monoxide in the presence of palladium chloride catalyst. Among the products formed are ethyl-3-butenoate and 3-butenoic anhydride. U.S. Pat. No. 3,437,676 to von Kutepow, et al. describes the reaction of allyl alcohol, carbon monoxide and water in the presence of a homogenous palladium complex such as bistriphenylphosphine palladium dichloride to provide carboxylic acids. U.S. Pat. No. 4,140,806 to Fernholz, et al. describes the reaction of an allyl compound substituted by oxygen functions, e.g., allyl alcohol, with carbon monoxide in the presence of a heavy metal catalyst such as elemental palladium and methyl iodide or palladium iodide as co-catalyst to provide vinylacetic acid. Patentees disclose that isometric $C_4$ acids, such as cis- and trans- crotonic acid, are not formed, or form in a small amount only, in contrast to known processes. U.S. Pat. No. 4,189,608 to Kurkov describes the reaction of allyl alcohol with carbon monoxide in the presence of a palladium chloride catalyst and in a substantially anhydrous $C_2$–$C_{10}$ carboxylic acid liquid solvent to provide 3-butenoic acid (i.e., vinylacetic acid).

SUMMARY OF THE INVENTION

It has now been discovered that allyl alcohol and carbon monoxide can be reacted, usually at elevated temperature and pressure, in the presence of a catalytically effective amount of a heterogeneous catalyst composition comprising zero valent palladium and a catalyst promoting amount of haloacid to provide a mixture of products predominantly made up of carboxylic acids containing four and five carbon atoms. Among such acids are 3-butenoic acid, crotonic acid, butyric acid, isobutyric acid, glutaric acid and methyl sussinic acid. In addition to the foregoing reaction products, smaller quantities of other oxygenated compounds may be produced such as glutaric anhydride, methyl succinic anhydride, allyl ether, allyl vinyl acetate, and so forth. Such compounds also posses utility as intermediates for the manufacture of a variety of industrially useful products.

Unlike many of the palladium-containing catalyst systems of the prior art which are soluble in the reaction medium, e.g., the palladium complex described by U.S. Pat No. 3,437,676 to von Kutepow, et al., the acid-promoted zero valent palladium catalysts of the present invention remain insoluble in the reaction mixture thereby greatly facilitating their separation from the reaction products and subsequent use for further carbonylation of allyl alcohol. Contrary to what one skilled in the art would expect based upon the disclosure of U.S. Pat. No. 4,140,805 to Fernholz, et al., substantial quantities of $C_4$ and $C_5$ acids result from the process of the present invention.

DESCRIPTION OF THE PREFERRED EMBODIMENTS

The process of the present invention contemplates the use of allyl alcohol and carbon monoxide in the commercially available grades, i.e., containing minor amounts of one or more impurities which do not appreciably interfere with the progress of the reaction herein. The molar ratios of allyl alcohol and carbon monoxide can vary widely, it generally being preferred to employ carbon monoxide in substantial molar excess, e.g., from about 1.5 to about 10 moles carbon monoxide per mole of allyl alcohol.

The palladium component of the catalyst is in the metal or, zero valent state, or, if in combined form such as palladium salt, is capable of undergoing reduction under the conditions of the reaction to provide zero valent palladium. The palladium can be used as a fine powder or, advantageously, supported upon a solid inert catalyst carrier such as carbon, silica, alumina, silica-alumina, zirconia, titania, quartz, glass beads, and the like. The zero valent palladium is employed in combination with a hydrogen halide, i.e., hydrogen fluoride, hydrogen chloride, hydrogen bromide, or hydrogen iodide, as catalyst promoter, generally at a molar ratio of HX:Pd of 10:1 to about 200:1 (X=Cl, Br or I). Hydrochloric acid is an especially preferred promoter.

The amount of palladium catalyst can vary over a wide range provided, of course, at least catalytically effective amount is employed. Thus, for example, from about 0.00001 to about 0.5, and preferably from about 0.01 to about 0.1, molar equivalents of zero valent palladium catalyst per mole of allyl alcohol can be used with good results.

Although carbon monoxide will react with allyl alcohol at room temperature and atmospheric pressure, reasonable reaction rates favor the use of temperatures and pressures which are substantially greater than those of the ambient surroundings. Accordingly, it is preferred to conduct the reaction at an eleveated temperature within the range of from about 80° C. to about 300° C. Within the lower end of this range, i.e., from about 80° C. to about 135° C., the reaction has been observed to provide a mixture for the most part containing 3-butenoic acid together with some diallyl ether and allyl esters. At the upper end of the temperature range, i.e., from about 150° C. to about 300° C., the reaction mixture will be largely that of crotonic acid, butyric acid, isobutyric acid, 3-butenoic acid, glutaric acid and methyl succinic acid. Pressures on the order of about 2,000 psig to about 5,000 psig, and especially about 2,500 psig to about 3,500 psig, are preferred.

The process of this invention is suitably conducted on a batch or continuous basis and contemplates the use of conventional high pressure equipment.

The following examples are further illustrative of the process of this invention.

EXAMPLE 1

Into a 70 ml Parr reactor was charged a mixture of 15 ml allyl alcohol, 05 g of 5% Pd on carbon and 0.87 g anhydrous hydrogen chloride. The reactor was pressurized with carbon monoxide at 3000 psi and sealed. The reactor was shaken in an oven heated at 85° C. for six hours. The reactor was cooled to room temperature and vented. The reaction mixture was filtered and analyzed. Chromatographic analysis indicated that the mixture contained (% by volume): 60% allyl 3-butenoate, 29% butenoic acid, 4% allyl ether and the balance being unconverted allyl alchol.

EXAMPLE 2

Example 1 was repeated, except the temperature was raised to 100° C. The analysis gave the composition (vol. %): 73% 3-butenoic acid, 22% allyl 3-butenoate, 2% allyl ether and the balance being unconverted allyl alcohol.

EXAMPLE 3

Example 1 was repeated, except the temperature was raised to 135° C. and the pressure was 2800 psi. Analysis disclosed presence (vol.%) of: 14% mixed glutaric and methyl succinic acids, 40% allyl 3-butenoate, 44% 3-butenoic acid and 2% ally ether.

EXAMPLE 4

Example 1 was repeated, except the temperature was raised to 150° C. using 0.43 g HCl with 0.62 g triphenylarsine as promotors. The reaction mixture contained (vol.%): 37% 3-butenoic acid, 10% isobutyric acid, 30% crotonic acid, 5% butyric acid and 18% mixed glutaric and methyl succinic acids.

EXAMPLE 5

Example 4 was repeated without triphenylarsine and the temperature was raised to 175° C. at 2850 psi CO. The reaction mixture separated into two layers. Analysis of the upper layer disclosed presence of (vol.%): 38% 3-butenoic acid, 7% isobutyric acid, 6% butyric acid, 35% crotonic acid and 13% mixed glutaric and methylsuccinic acids.

EXAMPLE 6

Example 5 was repeated except that 0.29 g HCl was used. The reaction mixture contained (vol.%): 45% 3-butenoic acid, 6% isobutyric acid, 4% butyric acid, 31% crotonic acid and 13% mixed glutaric and methylsuccinic acids.

As the results of the foregoing examples show, the composition of the reaction products is influenced by the reaction temperature with maximum quantities of $C_4$ and $C_5$ carboxylic acids being obtained at the higher temperatures.

What is claimed is:

1. The carbonylation process which comprises reacting allyl alcohol and carbon monoxide under carbonylation conditions substantially in the absence of water and in the presence of a catalytically effective amount of a catalyst composition containing zero valent palladium promoted with a catalyst promoting amount of a hydrogen halide selected from the group consisting of hydrogen fluoride, hydrogen chloride, hydrogen bromide and hydrogeniodide to provide one product or a mixture of products predominately made up of $C_4$ and $C_5$ carboxylic acids selected from the group consisting of vinylacetic acid, crotonic acid, butyric acid, isobutyric acid, glutaric acid and methyl succinic acid.

2. The process of claim 1 wherein the carbon monoxide is present in substantial molar excess compared to allyl alcohol.

3. The process of claim 2 wherein the carbon monoxide is present at about 1.5 to about 10 moles per mole of allyl alcohol.

4. The process of claim 1 wherein the zero valent palladium is supported on an inert carrier.

5. The process of claim 4 wherein the inert carrier is carbon.

6. The process of claim 1 wherein the promoter is present at a molar ratio of HX:Pd of from about 10:1 to about 200:1.

7. The process of claim 1 wherein from about 0.00001 to about 0.5 molar equivalents of zero valent palladium per mole of allyl alcohol are used.

8. The process of claim 7 wherein from about 0.01 to about 0.1 molar equivalents of zero valent palladium per mole of allyl alcohol are used.

9. The process of claim 7 wherein the reaction of allyl alcohol and carbon monoxide is carried out from about 80° C. to about 300° C.

10. The process of claim 1 wherein the reaction of allyl alcohol and carbon monoxide is carried out at about 80° C. to about 135° C. and the reaction produces one or more oxygenated products other than a $C_4$ carboxylic acid, said oxygenated products being selected from the group consisting of allyl ether, allyl vinyl acetate and.

11. The process of claim 9 wherein the reaction of allyl alcohol and carbon monoxide is carried out at about 150° C. to about 300° C.

12. The process of claim 1 wherein the reaction of allyl alcohol and carbon monoxide is carried out at from about 2,000 psig to about 5,000 psig.

13. The process of claim 12 wherein the reaction of allyl alcohol and carbon monoxide is carried out from about 2,500 psig to about 3,500 psig.

14. The process of claim 1 carried out substantially in the absence of oxidizing agent.

15. A process for making vinylacetic acid which comprises reacting allyl alcohol and carbon monoxide under carbonylation conditions substantially in the absence of water and in the presence of a catalytically effective amount of a catalyst composition containing zero valent palladium promoted with a catalyst promoting amount of a hydrogen halide selected from the group consisting of hydrogen fluoride, hydrogen chloride, hydrogen bromide and hydrogen iodide to provide said vinylacetic acid.

16. The process of claim 15 wherein the reaction of allyl alcohol and carbon monoxide is carried out at a temperature of from about 80° C. to about 135° C. and a pressure of from about 2,000 to about 5,000 psig.

17. The process of claim 15 carried out substantially in the absence of oxidizing agent.

18. A process for making a $C_4$ carboxylic acid selected from the group consisting of crotonic acid, butyric acid and isobutyric acid which comprises reacting allyl alcohol and carbon monoxide under carbonylation conditions substantially in the absence of water and in the presence of a catalytically effective amount of a catalyst composition containing zero valent palladium promoted with a catalyst promoting amount of a hydrogen halide selected from the group consisting hydrogen fluoride, hydrogen chloride, hydrogen bromide, and hydrogen iodide to provide said $C_4$ carboxylic acid.

19. The process of claim 18 wherein the reaction of allyl alcohol and carbon monoxide is carried out at a temperature of from about 150° C. to about 300° C. and a pressure of from about 2,000 to about 5,000 psig.

* * * * *

UNITED STATES PATENT AND TRADEMARK OFFICE
CERTIFICATE OF CORRECTION

PATENT NO. : 4,801,743
DATED : January 31, 1989
INVENTOR(S) : William D. Baugh and Jawad H. Murib It is certified that error appears in the above-identified patent and that said Letters Patent is hereby corrected as shown below:

Claim 1, line 9, the term "hydrogeniodide" should read ---hydrogen iodide---.

Claim 10, line 6, delete the "," appearing after "ether" and insert therefor ---and---; line 7, delete "and".

Claim 18, line 9, insert ---of--- after "consisting".

Signed and Sealed this

Fourteenth Day of August, 1990

Attest:

HARRY F. MANBECK, JR.

*Attesting Officer*  *Commissioner of Patents and Trademarks*